United States Patent [19]

Cohen

[11] Patent Number: 4,652,374

[45] Date of Patent: Mar. 24, 1987

[54] PROCESS FOR ANAEROBIC FERMENTATION OF SOLID WASTES IN WATER IN TWO PHASES

[75] Inventor: Alberto Cohen, Huizen, Netherlands

[73] Assignee: Gist-Brocades N.V., Delft, Netherlands

[21] Appl. No.: 648,194

[22] Filed: Sep. 7, 1984

[30] Foreign Application Priority Data

Sep. 9, 1983 [NL] Netherlands .......................... 8303129

[51] Int. Cl.$^4$ .............................................. C02F 11/04
[52] U.S. Cl. ...................................... 210/603; 210/613
[58] Field of Search ......................... 210/603, 612–614, 210/629, 622–626

[56] References Cited

U.S. PATENT DOCUMENTS

| | | | |
|---|---|---|---|
| 2,029,702 | 2/1936 | Bushwell et al. | 210/612 |
| 4,067,801 | 1/1978 | Ishida et al. | 210/603 |
| 4,185,680 | 1/1980 | Lawson | 210/603 X |
| 4,204,842 | 5/1980 | Morel et al. | 210/603 X |
| 4,252,901 | 2/1981 | Fischer et al. | 210/603 X |
| 4,318,993 | 3/1982 | Ghosh et al. | 435/299 |
| 4,400,195 | 8/1983 | Rijkens | 210/603 X |

FOREIGN PATENT DOCUMENTS

| | | |
|---|---|---|
| 2515205 | 4/1983 | France . |
| 2534274 | 4/1984 | France . |
| 1521609 | 8/1978 | United Kingdom . |
| 2013170 | 8/1979 | United Kingdom . |

Primary Examiner—Tom Wyse
Attorney, Agent, or Firm—Fleit, Jacobson, Cohn & Price

[57] ABSTRACT

A solid organic waste is fermented in water in two phases, a hydrolysis/acidification phase and a methane fermentation phase. Solid organic waste is introduced in the first phase, of which waste at least 80% of the volume has a particle size larger than x mm, x being between 0.25 and 1.5 mm dependent on the introduced solid organic waste. The waste in the first phase is continuously or periodically stirred and is screened for the removal of particles smaller than x mm with liquid, whereafter the smaller particles are separated from the liquid and the so-separated liquid is at least mainly supplied to the methane fermentation space, while the separated smaller particles are recirculated to the first phase reactor and/or discharged.

18 Claims, 3 Drawing Figures

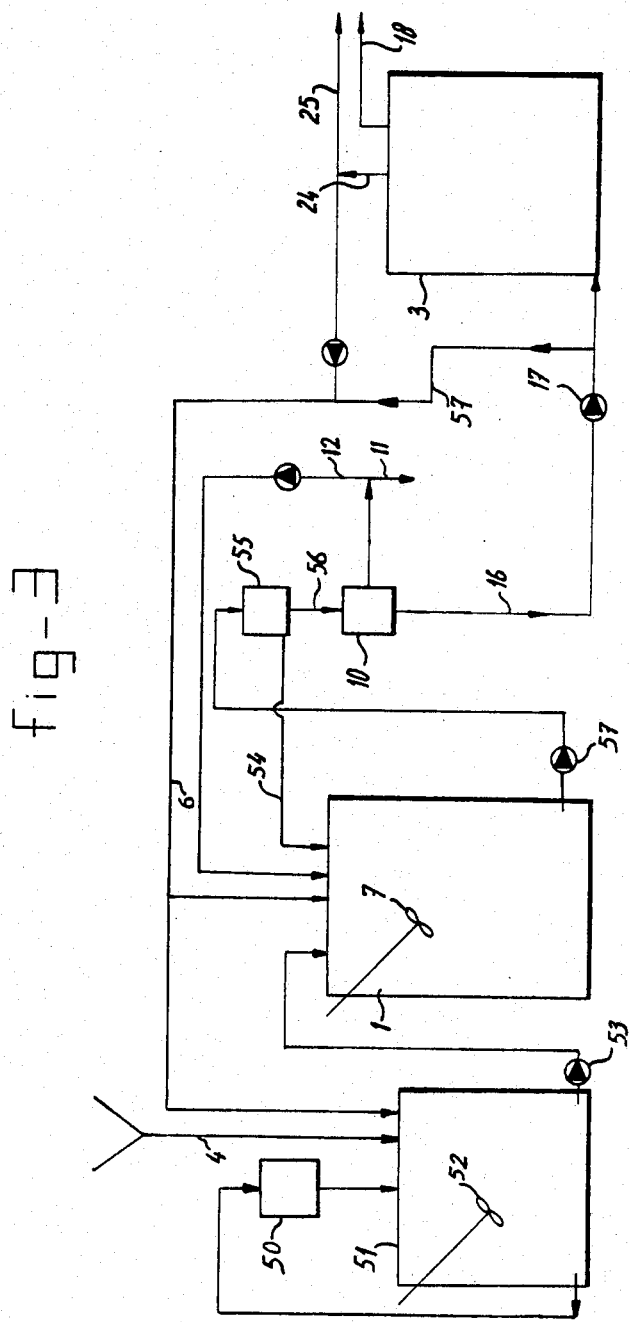

PROCESS FOR ANAEROBIC FERMENTATION OF SOLID WASTES IN WATER IN TWO PHASES

The invention is related to a process for the anaerobic fermentation of solid organic wastes in water in two phases, a hydrolysis/acidification phase and a methane fermentation phase, and to an apparatus for the performance of this process.

It is known to anaerobically ferment organic waste in two phases, namely in a first phase, in which hydrolysis and acidification take place, and in a second phase, in which methane fermentation takes place. For example it is known from the article of J. D. Keenan: Multiple Staged Methane Recovery from Solid Wastes, J. Environ. Sci. Health, A 11 (8&9), 525–548 (1976) to treat organic waste material is suspended condition in this way. All material is in this case transported from the first phase to the methane fermentation phase.

This system gives a good all-sided admittance of the liquid to the surface area of all waste particles and is especially suitable for waste consisting of small particles, such as in industrial and domestic waste water, including smaller quantities of proteins, carbohydrates and fat. For leaf-waste in larger particle form, waste of vegetables and fruits and for grasses this method is less suitable, because such material is allowed to be supplied to the apparatus only in strongly diminished form and in relatively small quantity in relation to the quantity of water to be able to keep the waste in suspension or has to stay with the coarser particles completely outside of the acidification phase and if necessary has to be subjected first to a separate hydrolysis, because when all materials from the first phase are aselectively transported to the methane fermentation step, this is not appropriate for a lot of fermentable wastes in view of the optimally required residence times in hydrolysis-/acidification phase and methane fermentation phase, respectively, and the possible suppression of methane bacteria but not hydrolysed parts such as lignocellulose residues, which are going to fill the methane fermentation space.

From the Dutch application No. 80.06567 it is known that predominantly solid organic waste is batchwise anaerobically digested by storing the waste as a substantially fixed-bed in a reaction vessel, percolation with liquid and leading the collected liquid to an auxiliary reactor where the fermented organic material is anaerobically converted into carbondioxide and methane while the effluent from the auxiliary reactor is sprayed again over the fixed waste bed in the reaction vessel. The residue left has to be removed from the reaction vessel. However, not all kinds of solid organic waste were found to be treated well in this way.

The latter system raises difficulties in view of the smooth percolation of the water through the solid material and by the inclination towards plugged in the bed over substantial parts of the content, with preferential paths of the water around it.

From the British patent application No. GB 2013170A it is known to ferment in two phases animal manure and particularly the manure of pigs. The animal waste is collected in a reactor cum sedimentation tank. During several days fermentation and settlement of the solid fraction occurs in this tank. The supernatant liquid is lead to an anaerobic digester, and the settled sludge is removed to be dried or disposed on land. This British patent application does not disclose the treatment of fruit and vegetable waste, grass or waste of agricultural products but is intended for the treatment of more diluted animal waste. Moreover the process of this British application is not very efficient because the contact between the solid waste and liquid is far from optimal, resulting in too long residence times.

The object of the invention is now to improve such known systems and more particularly to adapt them for voluminous waste, that naturally tends to plug during percolation. This waste contains at least a large part of material which fastly hydrolyses, like fruit- and vegetable waste, grass or other waste of agricultural origin and rather solid organic waste such as for example the organic part of domestic waste. These wastes may have a high percentage of cell-liquid, and more generally a liquid bound by the biological structure and/or enclosed by biological membranes. With the presently proposed system an improvement in capacity and efficiency of the equipment is attained.

As result of extensive research and experimentation a process could be found according to the present invention, characterized in that solid organic waste to be treated is introduced in a reaction space of the first phase, of which waste at least 80% of the volume has a particle size, larger than x mm, x being between 0.25 and 1.5 mm dependent on the solid organic waste introduced, and that the waste in that reaction space is continuously or periodically, stirred and is screened for the removal of particles smaller than x mm with liquid, whereafter the particles smaller than x mm are separated from the liquid and the so separated liquid is at least mainly supplied to the methane fermentation space, while the separated smaller particles are recirculated to the first phase reactor and/or discharged.

So a fast separation is obtained between not yet sufficiently fermented larger waste particles and compounds formed by fermentation and being dissolved as well as not-fermentable compounds, for example mineral components of the waste such as sand and clay. So the fact, that smaller particles of the organic waste are converted much faster in soluble compounds than larger particles because of their large surface area in relation to their volume, is optimally used to give the total amount of waste a residence time, in the hydrolysis/acidification space, adapted to the size of the waste particles.

As result of extensive experimentation it was found that the reduction of the organic wastes is strongly stimulated by the removal in question of liquid and fine solid particles from the hydrolysis/acidification space, so that that removed liquid cannot restrain the acidification. Hydraulic residence times of 0.1–2 days have appeared to be appropriate for the performance of the process and residence times of 0.5–1.5 days are preferred. In case of longer hydraulic residence times the hydrolysis/acidification will be slowed down because of the increase of the fatty acids concentration.

During one experiment the ash content of the solid particles, removed from the fermentation space by means of the screening, appeared to be increased from 22% for the starting material up to 44% for the material removed.

Stirring may be carried out in several manners. The process according to the invention may be carried out with strongly varying liquid contents in the hydrolysis-/acidification space in question, however the use of a liquid content enabling the use of normal liquid stirrers is preferred. According to a specific embodiment of the present invention the process comprises the operation in "dry" condition in that hydrolysis/acidification space and in that case such liquid stirrers are not considered. With the term "dry" condition as used throughout this specification is meant the condition in which a person skilled in the art would not choose normal liquid stirrers. For example when the process is performed with tomatoes normal liquid stirrers are applied, while in case of coarse sugar beet waste or carrots waste other kind of stirrers have to be used when no significant amount of aqueous liquid is added to the waste. Stirring in case of a "dry" condition may take place for example by lifting the waste with the help of a device from the lower part of that reaction space and at least partly recirculating the waste to the top of that reaction space and/or by using a mixer or other means suitable for stirring such a mass. This appears to give a moderate stirring, which is still sufficient to bring the total amount of waste in good contact with the liquid and to have the hydrolysis and acidification take place quickly in case of the "dry" process.

The effluent from the methane fermentation phase is preferably at least partly recirculated in such a way into the first phase reaction space (in the case of the "dry" condition), that without further supply of liquid to that reaction space except for the liquid present in the waste supplied, the percentage of aqueous liquid added to the waste is maintained in that reaction space when the preferred operation conditions are reached in this reaction space.

The screen surface for the removal of liquid and particles smaller than x mm may be situated above the waste in that reaction space, namely at choice inside or outside that reaction space, in addition to which the lifting device has to be constructed in such a way that it doesn't dewater the waste too much during the lifting till above the waste in that reaction space, so for example a screw pump or a centrifugal pump may be used.

It will be appreciated by people skilled in the art that the successfully applied type of device applied for the introduction of the waste in the first reaction space of the first phase is dependent on the condition of the introduced organic waste too.

It was found that when carrying out the invention with such a "dry" mass no difficulties concerning the percolation of the liquid through the solid organic waste were encountered.

Preferably aqueous liquid is added to the solid organic waste, to such extent that the mass in the reaction space of this first phase is much wetter than in the case of the "dry" process, in which case then normal stirrers suitable for stirring liquids can be applied. Fresh water and/or more preferably a part of the effluent from the methane fermentation reactor can be used by adding it to the solid organic waste, but also waste water can be used. Obviously when waste water is added, the waste water is of organic origin containing no inhibiting substance for the methane fermentation phase. Preferably the solid organic waste is mixed with the aqueous liquid before entering the hydrolysis/acidification space. The wet mass in that first reaction space may be obtained by addition of from 0-150 volume % of aqueous liquid added to the waste per bulk volume and more preferably 25-100 volume %. Preferably the effluent of the methane fermentation phase is recirculated at least partly in such a way into the first phase reaction space, that without further supply of liquid to that reaction space, except for the liquid present in the waste supplied, the percentage of aqueous liquid added to the waste is maintained in that reaction space when the preferred operation conditions are fulfilled in this reaction space. In this case normal liquid stirrers are considered for stirring the mass. The intended screening may take place through the openings of a screen surface, that formes a part of the wall of the treating space. More preferably the "wet" waste is pumped from the reaction space to a screening device provided with for example a fixed screen surface but of course other screening devices for example a vibrating screen or a drum screen may be considered. All kinds of pumps, which are able to transport the "wet" mass, can be used for example a centrifugal pump or a peristaltic hose pump.

The same transporter can be used at the same time to transport the material over a screen surface for the intended screening to recirculate part of the waste that did not get through the screen surface, as well as to remove the non-recirculated part of the waste from that treating space. The screen surface may be situated therefore above the waste in that reaction space, namely at choise inside or outside that reaction space.

The first phase may take place in more than one reaction space, which reaction spaces may therefore be connected in series or parallelly with regard to the flow of the waste.

Due to the desired construction of the collecting space under the screen surface it may be desirable, in view of the solid deposits in it, to flush this reaction space periodically or continuously. This is done by recirculating liquid, which is separated from the material that passed the screen, and/or by liquid from the methane fermentation space. By proper controlling of the relation between these flows and the total quantity of the flushing liquid, and so the extent in which liquid leaves the hydrolysis/acidification space and enters that collecting space, a proper control of the liquid flow to that methane fermentation space is possible as well. If that first phase is carried out in more than one reaction space in series connection in view of the solid material, then it is advisable to provide each of those reaction spaces with such a screen provided with a collecting space.

It will be appreciated that another feature of the present invention is formed by an apparatus for performing the process described before. Such apparatus is characterized firstly in that it comprises a reaction space, which serves for carrying out in it of a first phase or part of it of a two-phase-fermentation-system for solid organic waste, a screen with a screen surface with openings with a linear size or comparable screen-size of 0.25-.5 mm or with bars not more than 0.25-1.5 mm apart for the removal of liquid containing smaller solid particles to a collecting space, a separator for the separation of solid particles from that liquid and means to agitate the waste in that reaction space. The chosen size of the openings in the screen depends on the fermentation rate of the waste. In general, the better the waste degrades, the smaller the particals, and a screen surface provided with smaller openings can be applied within the above mentioned mesh range.

Moreover, the invention involves a number of embodiments and preferred features of that apparatus as will be described hereafter.

The invention will be elucidated into details on the basis of the annexed figures, which by way of example show a flowscheme according to the invention and possible embodiment of a part of an apparatus for the performance of the process in question.

Figure 1:
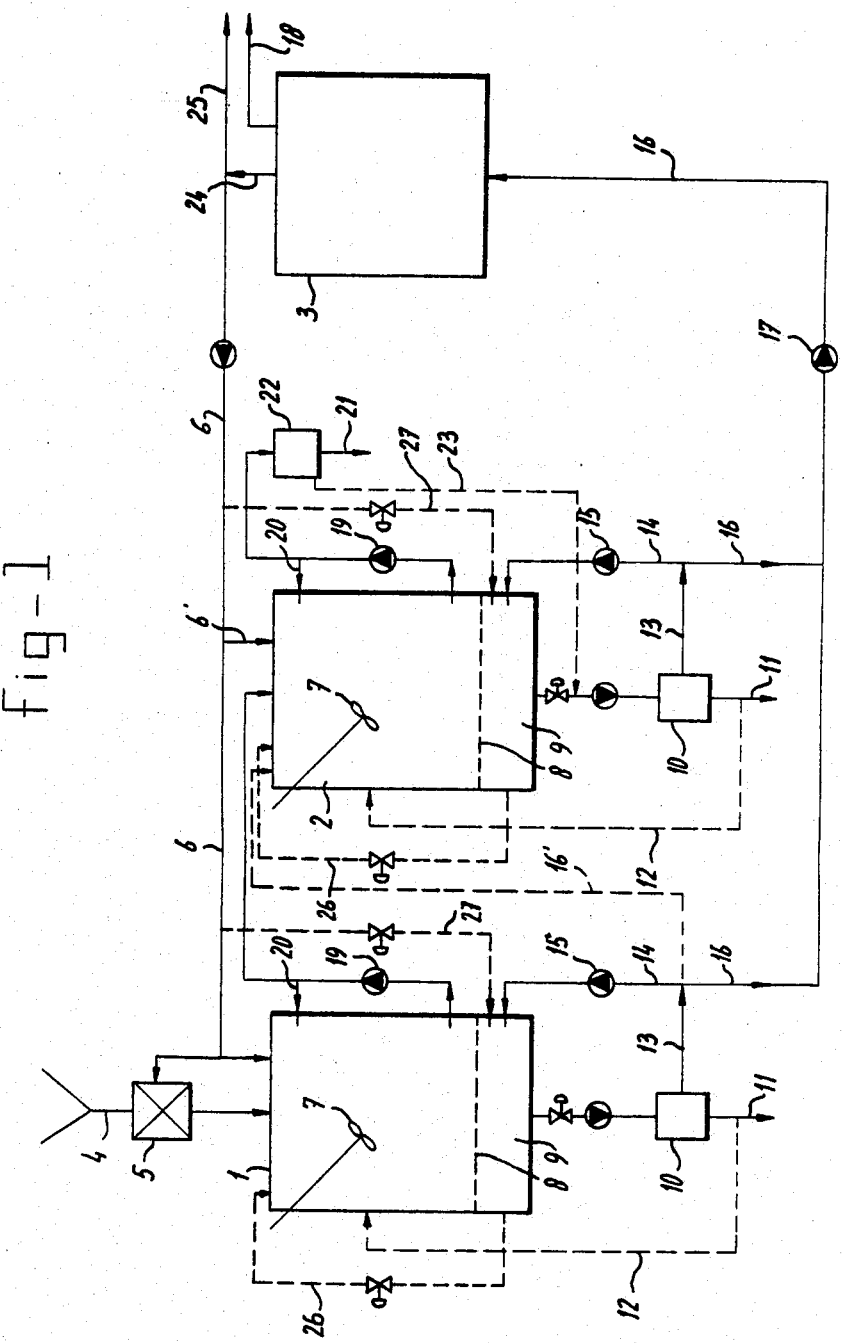
FIG. 1 shows such a flowscheme.

In the apparatus of FIG. 1 it is assumed that hydrolysis and acidification of the solid organic material take place in two in series or in parallel arrangement connected reaction spaces 1 and 2, which form together the first phase of the fermentation, while in a methane fermentation space 3 the second phase, the methane fermentation, is carried out with the decay products solubilized in the first phase.

Solid organic material is supplied, if desired with an adjusted quantity of liquid from a previous step and/or with added water and/or partly water of the effluent from the methane fermentation reactor, via feed line 4 to reaction space 1. If the organic waste contains a lot of big leafs or similar material, then it may be shredded in a shredding device 5. As shredding device may be used for example a chaffcutter or a pulveriser. Obviously the largest particle size allowed for the pumping of the waste to reaction space 1 depends mainly on the kind of pump used. Generally the largest particles allowed are between 1–5 cm. In reaction space 1 a part of the effluent from the methane reactor 3 is recirculated via inlet 6 as well. Obviously the supply of the aqueous liquid to the solid waste may take place in reaction space 1, or-/and before entering this reaction space, for example in the shredding device 5.

When the organic waste is obtained batchwise, the solid organic material may be shredded batchwise and transported to a buffer vessel from which it is continuously supplied to reaction space 1.

A schematically indicated stirring device 7 in each of the reaction spaces 1 and 2 may provide the agitation of the solid material in those reaction spaces.

Each reaction space 1, 2 has a screen surface 8, which separates that reaction space from a collecting space 9, in which only liquid and smaller solid particles are allowed to enter. The screen surfaces 8 have for example a smallest linear size (for example width of the screen slits) or diameter of the openings of 1 mm. Obviously the screening device may be situated above or close to reaction space 1 too, in which case all kinds of screening devices can be used.

According to an embodiment of the invention a closed reaction vessel may be used for reaction space 1, 2 and in that case this reaction vessel has to be provided with a gas outlet for the removal of carbon dioxide and in a minor amount methane, formed during the hydrolysis/acidification step. A closed reactor can be used for example to prevent air pollution and/or cooling of the hydrolysis/acidification reactor.

The liquid containing those fine solid particles from each collecting space 9 is transported to a separator 10 which separates mainly the fine solid particles from the liquid, for example a filter or a screen such as a vacuum drum filter, a self-cleaning static screen or hydrocyclone or a combination of those devices. The separated solid particles can be removed at 11 as a thick sludge, in such condition that the sludge can be removed by a pump, and if it still contains rather a lot of not yet sufficiently fermented solid organic particles, it can be recirculated completely or partly through a conduit-pipe 12, drawn as an interrupted line, into the matching reaction space 1 or 2. The removed thick sludge may be dewatered and used for example as compost.

The liquid separated in the separator 10 is removed through an outlet 13. A part of this liquid can be pumped back through conduit-pipe 14 by means of pump 15 into the matching collecting space 9. The remaining liquid is transported through conduit-pipe 16 and pump 17 into the methane reactor 3 to be subjected to the methane fermentation. If desired, part of the liquid transported through conduit-pipe 16 may not be led to the methane fermentation reactor 3 but is directly recirculated via conduit-pipe 6. This recirculation conduit-pipe is not drawn in FIG. 1. The gas generated in the methane reactor is removed through conduit-pipe 18, is collected and is used for example as fuel.

It will be appreciated by everyone skilled in the art that any suitable methane fermentation reactor can be used in the present process, such as a UASB reactor, a fluidized-bed reactor, an anaerobic filter or a dow-flow stationary fixed film process. When for example a methane fermentation reactor is chosen in which excessive sludge is produced, this reactor is of course provided with an outlet for this excessive sludge.

Two or more hydrolysis/acidification reactors which are connected in series could be applied if a fastly decomposing waste has to be fermented. In the beginning all the waste is transported into reaction space 1 while that part of the slowly decomposing waste is transported to the next reaction space. The advantage of such system is that the liquid flow and so the hydraulic residence times of these reactors can be optimalized.

The waste treated in reaction space 1 is transported by appropriate transporters 19 out of reaction space 1 into reaction space 2. An adjustable part of that waste can be recirculated via a recirculation conduit-pipe 20 into reaction space 1. The transporters 19 and that conduit-pipe 20 can be situated in such a way (for example partly in reaction space 1), that they agitate the waste in it completely instead of, or in addition to stirrer 7.

The material from reaction space 2 can be removed in a similar way to that from reaction space 1, via transporters 19 provided with an adjustable recirculation-pipe. If reaction space 2 is the last reaction space, in which the organic waste itself is fermented, then transporters 19 of that reaction space can lead outside to an outlet 21. Because this waste may still contain rather a large fraction of water, it may be passed over a screen 22, for example over a self-cleaning static screen, from which the separated liquid may be transported through conduit-pipe 23 to the supply of the separator 10 matching that reaction space.

The conduit-pipe 16 of reaction space 2 to the methane reactor 3 combines with the conduit-pipe 16 of reaction space 1. Instead, an arrangement of reaction spaces 1 and 2 connected in series can be applied as well, if further acidification is desired, by connecting outlet 13 of separator 10 of reaction space 1 not with conduit-pipe 16 directly to the methane reactor 3 but with a conduit-pipe 16', which leads the liquid in question into reaction space 2. Conduit-pipe 6 has to lead then the effluent of the methane reactor alone or for the greater part into reaction space 1 and not or only in very small amounts into reaction space 2, so that the connection 6' of conduit-pipe 6 with reaction space 2 can be excluded or can be closed completely or almost completely.

The liquid treated in the methane reactor 3 is removed from there through conduit-pipe 24. A part of it is removed through outlet 25 from the system and another part is supplied through conduit-pipe 6 in a mutually adjustable distribution to the reaction spaces 1 and 2 and/or to the solid organic waste before entering reaction space 1. If the process is carried out with a lot of waste water, to be treated in the feed, then the return of effluent from the methane reactor 3 to the reaction spaces 1 and 2 may either be totally omitted, or take place in much smaller degrees.

Interrupted lines 26 indicate how the liquid can be recirculated from the collecting spaces 9 into the machining reaction spaces 1 or 2, adjusted by a valve, at choice to be opened and closed and if necessary by means of a pump if this flow doesn't take place by natural suppression in the desired degree. The collecting spaces 9 may, instead of or besides being flushed with liquid separated at 10, be flushed with liquid from the methane reactor 3, which can be supplied to those reaction spaces through drainings 27 of conduit-pipe 6. It is however also possible to flush those collecting spaces not at all, provided that they are appropriately constructed, for example with adequately steep walls and bottom.

As is described, the process according to the invention may be performed with a rather dry waste mass in reaction spaces 1 and 2 or with a substantially wetter mass.

Figure 2:
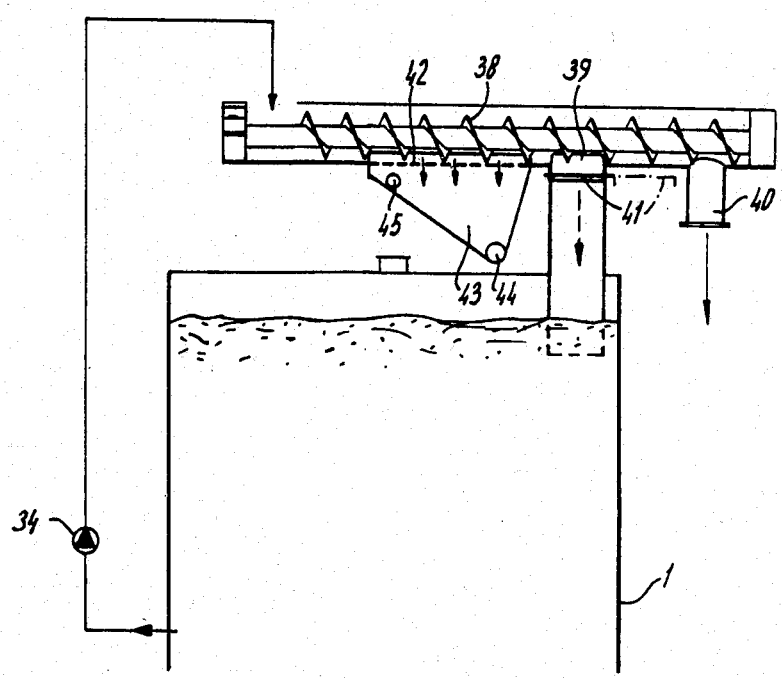
FIG. 2 shows a vertical cross section through a part of the apparatus for the performance of the first phase of a two-phase fermentation referred to in the elaborated presentation.

The equipment according to FIG. 2 shows a part of the described reaction space 1 in vertical cross section.

A pump 34 close to or in reaction space 1 lifts up the waste from reaction space 1 to a horizontal transporter 38, consisting of a worm-screw in a closed trough, which screw may be driven by an electric motor. That trough has two openings 39 and 40 in the bottom, of which opening 39 is changeable in size by a slide valve 41 and debouches above reaction space 1, while opening 40 discharges material to a trough, which leads into the top of reaction space 2 of FIG. 1. In this manner an adjustable part of the waste treated in reaction space 1 can be recirculated by transporter 38 into reaction space 1, while the rest is transported by that transporter to reaction space 2. In case of continuously opened slide valve 41, all the waste containing the particles larger than x mm are returned through opening 39 into the matching reaction space.

Reaction space 2 can be equipped with similar transporters, which are able to lift the waste, to enable the waste to fall back into reaction space 2 in controllable quantity through an opening such as 39 and can discharge it from that reaction space 2 through an opening such as 40, while it may be dewatered on a screen 22 (FIG. 1) as described with FIG. 1.

Until the horizontal transporter 38 makes the solid material reach the openings 39 and 40 in the bottom of the trough, it transports the material over a screen surface 42 with openings between 0.25-1.5 mm as described, which screen surface takes over the function of the screen surface 8 of FIG. 1. This screen surface 42 connects smoothly with the remaining bottom of the trough of transporter 38. It may be half-circular or totally circular, in which case, if desired, it may be rotated around its axis in a direction opposite to the rotation direction of jack-screw 38, in order to allow an automatical cleaning. Below this screen surface a screen collecting space 43 with oblique walls and an outlet at 44 at the bottom is situated. Such a collecting space will normally sufficiently empty itself to the separation device 10 of FIG. 1, but if desired here also may be flushed by liquid as well, separated in that device 10 (conduit-pipe 14 in FIG. 1) and/or by liquid, originating from the methane fermentation space 3 (conduit-pipes 6 and 27 of FIG. 1) (inlet 45).

EXAMPLE 1

In an apparatus according to the flow scheme as schematically shown in FIG. 3, a mixture of different vegetable wastes was fermented. The acidification/hydrolysis reaction space 1 was closed at the top and the gas production in this reaction space could be measured via an outlet (not drawn). The vegetable waste consisted amongst other things mainly of cucumber, lettuce, endive, celeriac, carrots, red beets, cabbage and tomatoes. The organic waste was originating from a vegetable auction. The results given are an average taken over five consecutive days. In those five days, 29,290 kg of organic waste corresponding with 30 $m^3$ liquid volume or 60 $m^3$ bulk volume was fermented. that waste was converted into 505 $m^3$ gas, consisting of 80% methane, in the methane fermentation space 3 (FIG. 3), which gas could be used as fuel. As methane fermentation reactor a UASB reactor was used. The total effluent was 30 $m^3$ of aqueous liquid and was discharged via outlet 25. The volume of the remaining solids, having a particle size smaller than 0.5 mm, was about 0.5 $m^3$ and was removed via conduit-pipe 11. After drying in a filter press this material could be suitable as compost.

The flows through the process during the mentioned five days were as follows. Via feed pipe 4, 12 $m^3$ bulk volume/day of waste was introduced in a reaction space 51. Reaction space 51 is provided with a cutting mixer 52 and a desintegrater pump 50. At the same time 5 $m^3$/day of aqueous liquid orginating from methane fermentation space 3 and separator 10 was introduced in reaction space 51. Pump 53 transported the mixture from reaction space 51 to the acidification space 1. Apart from the recirculated mass from screeening device 55 via conduit-pipe 54 (2.2 $m^3$/h), part of the separated particles in separator 10 via conduit-pipe 12 (0.1 $m^3$/day), part of the effluent of the methane fermentation and part of the separated liquid in separator 10 is lead (3.3 $m^3$/h) via conduit-pipe 6 to the reaction space 1. A device as shown in FIG. 2 is used for the screening-/recirculation of the mass pumped by pump 57 (6.2 $m^3$/h). As separator 10 a self-cleaning static screen is applied. The liquid (4.0 $m^3$/h) that leaves the separator is partly (2.9 $m^3$/h) pumped with pump 17 to the methane fermentation reactor and partly (1.1 $m^3$/h) recirculated via conduit-pipes 57 and 6 to reaction space 51 and to the hydrolysis/acidification space 1. In the methane fermentation space the liquid that enters this reaction space (2.9 $m^3$/h) is converted into effluent that is recirculated (2.65 $m^3$/h) via conduit-pipe 6, effluent that is removed from the system (0.25 $m^3$/h) via conduit-pipe 25, gas used as fuel (101 $m^3$/day) via conduit-pipe 18 and only small amounts of excessive effluent.

In this example the hydrolysis/acidification reactor was fed with 9.5 kg dry solids/$m^3$ day.

COD-values were determined for the volatile and suspended solids together (mix) as well as just the volatile solids after centrifugation (cen). For the effluent leaving the methane fermentation reactor via conduit-pipe 25 the following values were measured:

CODmix=2003 mg/l
CODcen=330 mg/l

For the effluent leaving the hydrolysis/acidification reactor via pump 57:

CODmix=7031 mg/l
CODcen=3457 mg/l

EXAMPLE 2

The same apparatus as in example 1 was used. In this example beet waste, viz. the ends of the bottom parts of the beets and the remaining parts of leafs of sugar beets, were fermented. The results show the average values over a periode of 22 days.

About 5 m$^3$ bulk volume/day (3 m$^3$ liquid volume/day), corresponding with 3209 kg/day and 401 kg dry solids/day, of beet waste was introduced in the process. From the hydrolysis/acidification reactor 92 m$^3$/day was pumped by pump 57. From this 60 m$^3$/day was introduced in the methane fermentation space, the remaining was recirculated via screening device 55, separator 10 or conduit-pipe 57. From the effluent of the methane fermentation space about 3 m$^3$/day was removed via conduit-pipe 25, while 57 m$^3$/day was recirculated. The gas production of the hydrolysis/acidification reactor was 10 m$^3$/day mainly consisting of carbon dioxide and only about 20% methane, the gas production in the methane fermentation reactor was 99 m$^3$/day (79% methane and 21% carbon dioxide). The residue flow discharged via conduit-pipe 11 was 383 kg/day containing 15% dry solids.

For the effluent leaving the methane fermentation reactor via conduit-pipe 25 the following values were measured:

COD$_{mix}$=2737 mg/l
COD$_{cen}$=490 mg/l
Kjeldahl-N$_{mix}$=273 mg/l
Kjeldahl-N$_{cen}$=59 mg/l
NH$_4$-N$_{mix}$=79 mg/l For the effluent leaving the hydrolysis/acidification reactor via pump 57:

COD$_{mix}$=6102 mg/l
COD$_{cen}$=3667 mg/l
Kjeldahl-N$_{mix}$=273 mg/l
Kjeldahl-N$_{cen}$=33 mg/l
NH$_4$-N$_{mix}$=51 mg/l The total conversion on dry solid base is 87.4%, the total conversion on weight base is 89.5%.

I claim:

1. A process for the anaerobic fermentation of solid organic wastes in water in a first hydrolysis/acidification phase and a second methane fermentation phase, said process comprising the steps of:
   introducing said solid organic waste into a reaction space of the first phase, at least 80% of the volume of said organic waste having a particle size larger than X mm, X being between 0.25 and 1.5 mm depending on the solid organic waste introduced;
   continuously or periodically stirring said organic waste;
   screening said organic waste for the removal of particles smaller than X mm with liquid;
   separating the particles smaller than X mm from the liquid;
   supplying said liquid from said separation step to said methane phase; and
   recirculating said separated smaller particles to said first phase reaction space.

2. Process according to claim 1, characterized in that the solid organic waste to be treated is continuously introduced in the reaction space of the first phase.

3. Process according to claim 1 characterized in that the waste, which has to be fermented, is successively transported through at least one reaction space wherein at least a part of the first phase is performed.

4. Process according to claim 1, characterized in that in the reaction space of the first phase aqueous liquid is added.

5. Process according to claim 4, characterized in that the solid organic waste is mixed with at least a part of that aqueous liquid before entering the first phase.

6. Process according to claim 4, characterized in that the aqueous liquid is totally or partly originating from the effluent of the methane fermentation phase.

7. Process according to claim 4, characterized in that the aqueous liquid is totally or partly waste water of organic origin containing no inhibiting substance for the methane fermentation phase.

8. Process according to claim 1, characterized in that particles smaller than x mm separated from the liquid are at least partly recirculated to the reaction space of the first phase.

9. Process according to claim 1, characterized in that at least in the first reaction space of the first phase the volume percentage of aqueous liquid added to this reaction space is 0–150% per volume of bulk waste.

10. Process according to claim 9, characterized in that this volume percentage of aqueous liquid added to this reaction space is 25–100% per volume of bulk waste.

11. Process according to claim 9, characterized in that the effluent of the methane fermentation phase is recirculated at least partly in such a way, that recirculated effluent is introduced in the reaction space of the first phase and the organic waste content is maintained in that reaction space.

12. Process according to claim 1, characterized in that the screening of the waste takes place on the screen surface situated mainly above the waste in that reaction space.

13. Process according to claim 12, characterized in that a transporter transports the waste over a screen surface, over an opening variable in size through which a determined part of the waste or the total waste, transported by that transporter, is recirculated in that reaction space, dependent on the size and/or the periodes of opening of that opening, and removes at the same time the remaining part of the waste.

14. Process according to claim 1, characterized in that the collecting space for the liquid which is separated during the screening of said organic waste, is periodically or continuously flushed by liquid.

15. Process according to claim 14, characterized in that said collecting space for the liquid is flushed by the effluent from the methane fermentation space.

16. Process according to claim 14, characterized in that said collecting space for the liquid is flushed by liquid which, during the separation of the smaller solid particles and the liquid, is separated from the material that has passed the screen surface.

17. A process according to claim 1 wherein said separated smaller particles are discharged.

18. A process according to claim 1 wherein said separated smaller particles are recirculated to said first phase reaction space and discharged.

* * * * *